(12) United States Patent
Pacino, Jr. et al.

(10) Patent No.: US 6,394,804 B1
(45) Date of Patent: May 28, 2002

(54) ARTICULATOR FOR DENTAL CASTS

(75) Inventors: Nicholas R. Pacino, Jr.; Terry L. Jackson, both of St. Louis, MO (US)

(73) Assignee: J&P Group, LLC, St. Louis, MO (US)

( * ) Notice: Subject to any disclaimer, the term of this patent is extended or adjusted under 35 U.S.C. 154(b) by 0 days.

(21) Appl. No.: 09/826,184

(22) Filed: Apr. 4, 2001

(51) Int. Cl.[7] ............................................. A61C 11/00
(52) U.S. Cl. ......................................... 433/64; 433/57
(58) Field of Search ............................. 433/57, 58, 59, 433/60, 61, 62, 63, 64, 65, 66, 67

(56) References Cited

U.S. PATENT DOCUMENTS

| | | | | |
|---|---|---|---|---|
| 1,654,453 A | * | 12/1927 | Brown | 433/58 |
| 3,126,632 A | * | 3/1964 | Weissman | 433/60 |
| 4,382,787 A | | 5/1983 | Huffman | 433/64 |
| 4,449,930 A | | 5/1984 | Huffman | 433/64 |
| 4,533,323 A | | 8/1985 | Huffman | 433/64 |
| 4,548,581 A | | 10/1985 | Huffman | 433/64 |
| D286,179 S | | 10/1986 | Huffman | D24/10 |
| D286,436 S | | 10/1986 | Huffman | D24/10 |
| 4,734,033 A | | 3/1988 | Huffman | 433/60 |
| 5,046,949 A | * | 9/1991 | Richardson | 433/57 |
| 5,425,636 A | * | 6/1995 | Ghim | 433/64 |
| 5,622,497 A | * | 4/1997 | Cho | 433/60 |

* cited by examiner

*Primary Examiner*—John J. Wilson
(74) *Attorney, Agent, or Firm*—Polster, Lieder, Woodruff & Lucchesi, L.C.

(57) ABSTRACT

An articulator for positioning a pair of dental casts relative to each other is disclosed which comprises a pair of members adapted to being connected to each other for pivotal movement relative to each other, each member comprising a central portion having a hooked end and a forked end with the forked end having an outer tine, an inner tine and a pin connected between the tines, and a ball connected to the central portion by a spline.

20 Claims, 2 Drawing Sheets

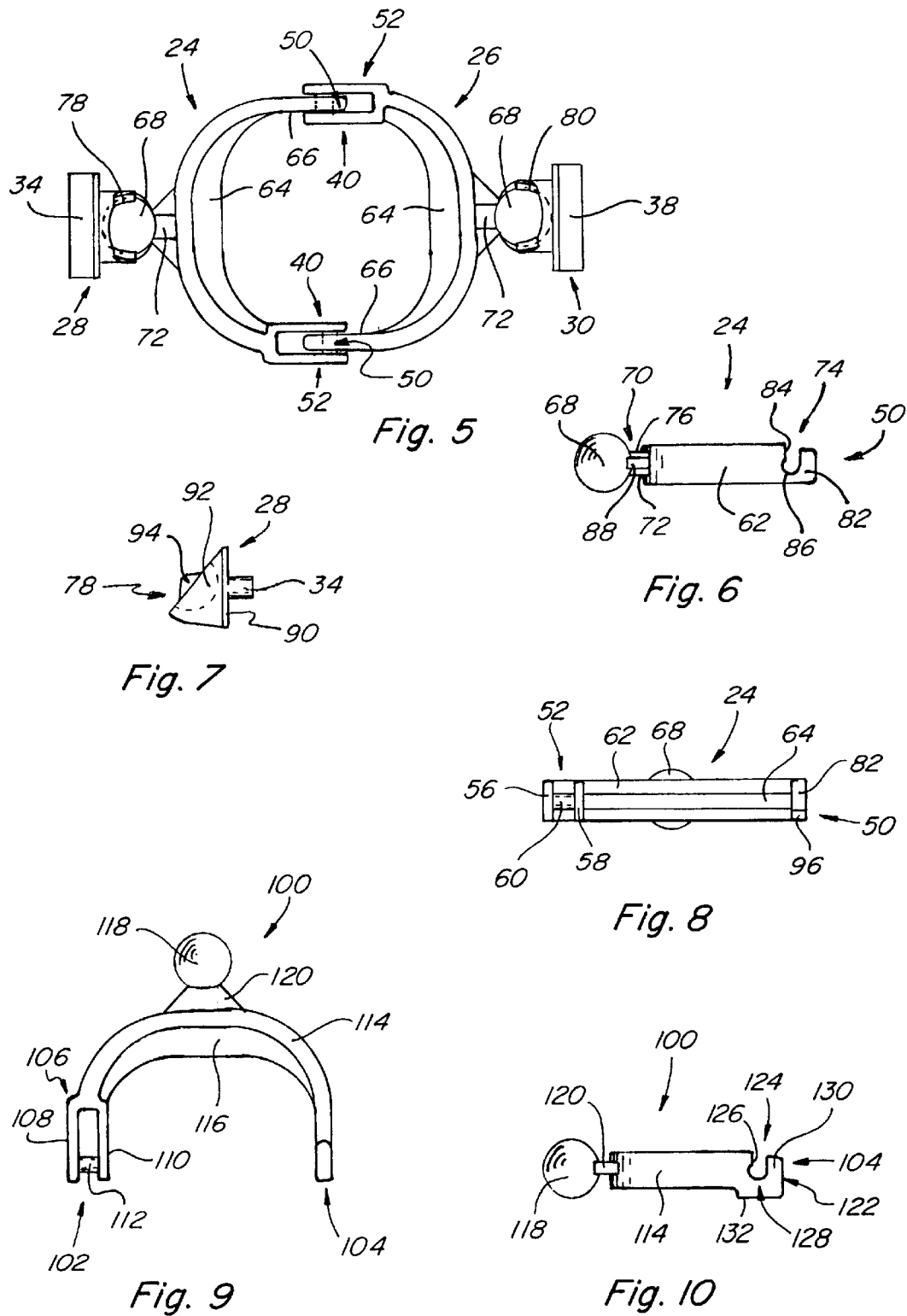

US 6,394,804 B1

ARTICULATOR FOR DENTAL CASTS

BACKGROUND OF THE INVENTION

This invention relates to an articulator used in conjunction with dental casts, and more particularly, to an articulator for dental casts which does not slidably disengage during use or operation.

Articulators are used in conjunction with casts of a dental model in order for a technician to develop, construct, or form prosthetic dentures or other denture elements. A dentist makes the dental casts of both the upper and lower jaws by using any well known casting methods. The technician uses these casts to shape or fit the denture elements in order to correct any dental problems. The articulator is attached to both of the dental casts. Once attached, the articulator is used to simulate the movement of the jaws relative to each other and the technician uses this movement to confirm proper registration or fit of the denture elements. It is important for the articulator to be able to allow the casts to move in all directions in order for the technician to verify the correctness of the dentures. For example, the articulator needs to be able to allow movement of the casts in order to confirm the registration of all opposed dental surfaces. Articulators have been constructed or formed of different materials and different details of construction. Known articulators range from simple designs to complex mechanical designs. Such articulators also range in price from inexpensive to expensive. One known articulator device has a snap fit hinge construction for disassembly and assembly of the articulator. However, due to the snap fit hinge design, the articulator is prone to come apart or disassemble during use. When a technician is working with the dental casts this should be avoided. Further, known articulators are not symmetrical in design and when dental casts are connected to the articulator the orientation of the articulator is not aesthetic.

The present invention is designed to obviate and overcome many of the disadvantages and shortcomings associated with presently available articulators. In particular, the present invention is an articulator which is designed and constructed to prevent against coming apart or disassembly during use. Moreover, the articulator of the present invention can be employed to construct dental devices and to register such devices in an accurate manner and alignment. Further, the articulator of the present invention is symmetrical in design and construction and when dental casts are attached to the articulator the orientation of the articulator is aesthetic.

SUMMARY OF THE INVENTION

In one form of the present invention, an articulator for positioning a pair of dental casts relative to each other comprises a pair of members adapted to being connected to each other for pivotal movement relative to each other, each member comprising a central portion having a hooked end and a forked end with the forked end having an outer tine, an inner tine and a pin connected between the tines, and a ball connected to the central portion by a spline.

In another form of the present invention, an articulator for positioning a pair of dental casts relative to each other comprises a pair of members adapted to being connected to each other for pivotal movement relative to each other, each member comprising a central portion having a hooked end and a forked end with the forked end having an outer tine, an inner tine and a pin connected between the tines, the hooked ends for connecting to the pins of the forked ends, a ball connected to each of the central portions by a spline, and a reinforcing rib positioned on the central portion, the reinforcing rib spanning between the inner tine and a point prior to the hooked end.

In yet another form of the present invention, an articulator for positioning a pair of dental casts relative to each other comprises a pair of members adapted to being connected to each other for pivotal movement relative to each other, each member comprising a central portion having a hooked end and a forked end with the forked end having an outer tine, an inner tine and a pin connected between the tines, the hooked ends for connecting to the pins of the forked ends, the central portion further comprising a reinforcing rib which spans between the inner tine and a point prior to the hooked end, and a ball connected to each of the central portions by a spline with the ball being centered on the member.

In light of the foregoing comments, it will be recognized that a principal object of the present invention is to provide an articulator which is of simple construction and design and which can be easily employed with highly reliable results.

Another object of the present invention is to provide an articulator that is easy to use and may be moved or operated through a large degree of motion or movement.

A further object of the present invention is to provide an articulator which is used to prepare and construct a dental appliance or restoration.

A still further object of the present invention is to provide an articulator which does not easily come apart or slide apart during use or operation.

Another object of the present invention is to provide an articulator which simulates jaw movement in order for a technician to construct a dental appliance and to verify proper alignment of the dental appliance.

A further object of the present invention is to provide an articulator which is strong and flexible and of unitary construction.

A still further object of the present invention is to provide an articulator which is strong, is reinforced, and symmetrical.

These and other objects and advantages of the present invention will become apparent after considering the following detailed specification in conjunction with the accompanying drawings, wherein:

BRIEF DESCRIPTION OF THE DRAWINGS

FIG. 5 is a top view of the articulator of the present invention with a pair of mounts positioned on the articulator;

FIG. 6 is a side view of the member of the articulator shown in FIG. 4;

FIG. 7 is a side view of one of the mounts shown in FIG. 5;

FIG. 8 is a front side view of a member of the articulator shown in FIG. 3;

FIG. 9 is a bottom view of another preferred embodiment of one member of an articulator constructed according to the present invention; and FIG. 10 is a side view of the member shown in FIG. 9.

DETAILED DESCRIPTION OF THE PREFERRED EMBODIMENTS

Figure 1:
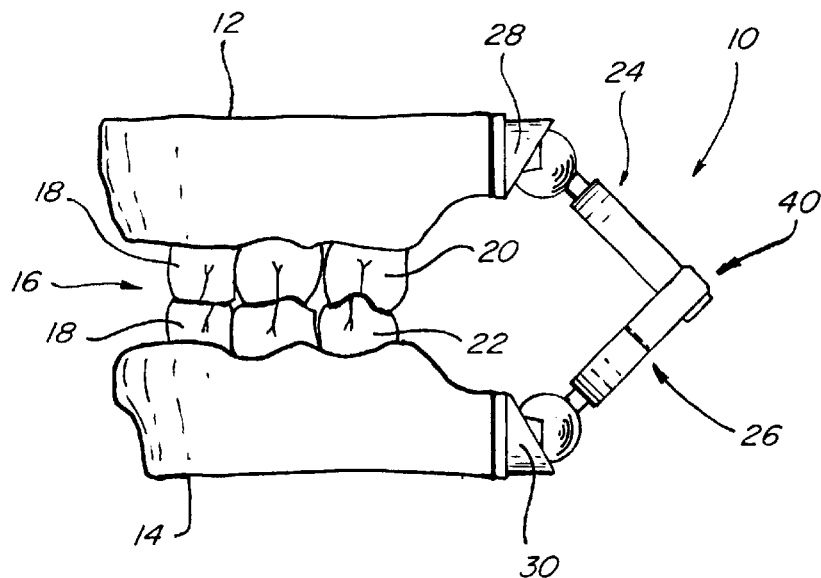
FIG. 1 is a side view of a preferred embodiment of an articulator constructed according to the present invention with the articulator being mounted to a pair of dental molds.

Referring now to the drawings, wherein like numbers refer to like items, number 10 identifies a preferred embodiment of an articulator 10 constructed according to the present invention. With reference now to FIG. 1, the articulator 10 is shown mounted to a pair of dental casts 12 and 14. The dental casts 12 and 14 are used to simulate a mouth 16 of a model, such as a person who needs to have dentures or other dental appliances. The mouth 16 can include teeth 18 which simulate the teeth 18 of a model. Additionally, the mouth 16 may a tooth 20 which may be a prosthetic tooth composed of a synthetic material such as gold or porcelain. The tooth 20 must be configured and shaped to naturally mate with or align with a tooth 22. The tooth 22 may be a simulation of an actual tooth in the mouth of a person with which the tooth 20 must contact. The casts 12 and 14 may be formed of any known casting material used for making such casts 12 and 14. Further, the teeth 18 and 22 are cast from the same material.

Figure 2:
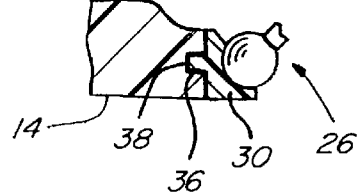
FIG. 2 is a partial cross-sectional side view of the articulator shown in FIG. 1 being mounted to a pair of dental molds.

The articulator 10 is shown to be comprised of a pair of interconnecting members 24 and 26 which are positioned within a pair of mounting members 28 and 30, respectively. The members 24 and 26 are free to move or rotate within the mounting members 28 and 30, as will be explained herein. Referring now to FIG. 2, the cast 12 has a groove 32 which is used to capture or hold a tongue portion 34 of the mounting member 28. The cast 14 also has a groove 36 which is adapted to receive a tongue portion 38 of the mounting member 30. The members 24 and 26 are capable of pivoting relative to each other at a pivot point 40 (FIG. 1), which is the point at which the members 24 and 26 are connected to each other.

As can be appreciated, the casts 12 and 14 may be moved relative to each other in order to simulate the movement of a person's jaws. By use of the articulator 10, the tooth 20 can be viewed to determine if the tooth 20 will impact or mate with the tooth 22 in order for a technician to verify the correctness of the tooth 20. If it is determined that the teeth 20 and 22 are not mating correctly, then the technician can make adjustments or alterations to the tooth 20. The articulator 10 also allows the technician to move or rotate either of the casts 12 or 14 apart from each other in order to view the tooth 20.

Figure 3:
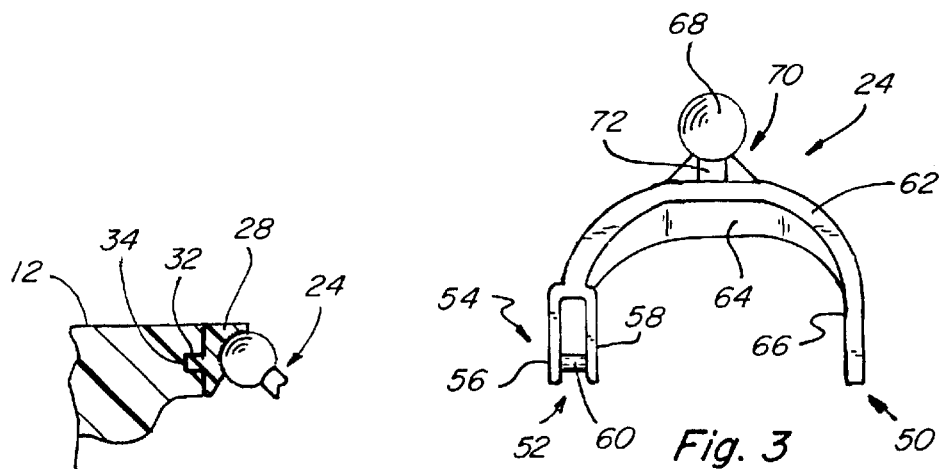
FIG. 3 is a top view of one member of the articulator constructed according to the present invention.

Referring now to FIG. 3, a top view of the member 24 of the articulator 10 is shown. The member 24 is generally C-shaped and may be constructed from a resilient flexible material, such as plastic. The member 24 has a first end 50 and a second end 52. The second end 52 comprises a forked end or fork member 54 having an outer tine 56 and an inner tine 58 with a pin portion 60 positioned between the tines 56 and 58. The member 24 further comprises a central portion 62 and a reinforcing rib 64. The rib 64 spans or runs from the inner tine 58 to a point 66 which is short of the end 50. In other words, the rib 64 is asymmetrical within the central portion 62. However, the rib 64 may be symmetrical within the central portion 62 or the rib 64 may span a distance which is less than the distance between the inner tine 58, the point 66, or the end 50. Additionally, the rib 64 may span the entire distance between the inner tine 58 and the end 50. Further, the width of the rib 64 is less than the width of the central portion 62. A ball or globe 68 is connected to the central portion 62 of the member 24 by use of a spline 70.

The spline 70 further has a centrally positioned upper reinforcing rib 72. The ball 68 is also positioned at a centrally located point on the central portion 62 of the member 24. Centering the ball 68 on the central portion 62 provides for an aesthetically pleasing device when the members 24 and 26 are connected together to form the articulator 10.

Figure 4:
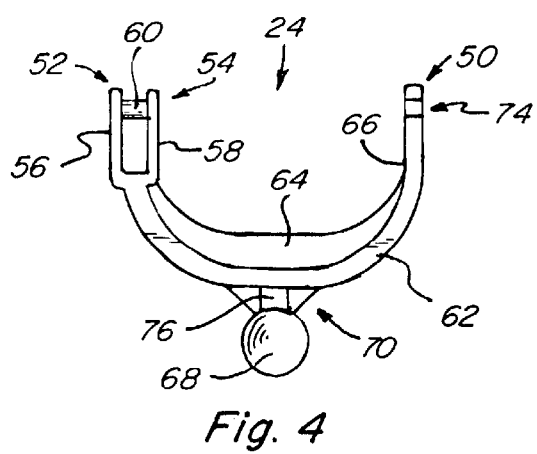
FIG. 4 is a bottom view of the member of the articulator shown in FIG. 3.

FIG. 4 illustrates a bottom view of the member 24 of the articulator 10. The member 24 is shown to have the fork portion 54 at the second end 52 with the fork portion having the outer tine 56, the inner tine 58, and the pin portion 60 between the tines 56 and 58. The pin portion 60 is shown being located toward the front of the tines 56 and 58. The first end 50 further has an opening or indentation 74 which is sized and shaped to receive the pin portion 60 of the other member 26. The spline 70, which connects the ball 68 to the central portion 62, also has a lower reinforcing rib 76. The central portion 62 and the reinforcing rib 64 are again depicted with the rib 64 running between the inner tine 58 to the point 66 which is prior to the end 50 and also prior to the indentation 74. Although not illustrated separately, the member 26 is a mirror image of the member 24 and the same numbers refer to like items.

With reference now to FIG. 5, the members 24 and 26 are shown connected together to form the articulator 10. As is shown, the first end 50 of the member 24 is connected to or hooked onto the pin portion 60 of the second end 52 of the member 26. Further, the first end 50 of the member 26 is connected to the pin portion 60 of the second end 52 of the member 24. The members 24 and 26 are also orientated in a manner that the top ribs 72 of each of the members 24 and 26 are on the same side. As can be appreciated, the bottom ribs 76 of each of the members 24 and 26 are on the opposite site in a view which is not illustrated in FIG. 5. The mounting members 28 and 30 are shown receiving the balls 68 of the respective members 24 and 26. The member 28 has a recess or cup portion 78 which is adapted to receive and retain the ball 68 of the member 24. The ball 68 is free to move or rotate within the cup portion 78 and is held in place by frictional engagement. The member 30 also has a cup portion 80 which receives and retains the ball 68 of the member 26. The cup portion 80 also allows the ball 68 of the member 26 to freely rotate or move therein. As discussed previously, the tongue portions 34 and 38 of their respective mounting members 28 and 30 are adapted to be inserted into the grooves 32 and 36 of the dental casts 12 and 14. The articulator 10 is capable of pivoting about the points 40, which are the connection between the first end 50 and the second end 52. The articulator 10 is also capable of rotating about the balls 68 and the cup portions 78 and 80. In this manner, a large range of motion is capable with the use of the articulator 10.

FIG. 6 illustrates a side view of the first end 50 of the member 24. The first end 50 has a hooked end or hook portion 82 having the opening 74. The opening 74 further has a retaining ledge or portion 84 which is used to capture and retain the pin portion 60 of the second end 52. The opening 74 of the hook portion 82 has a bottom 86 which is arcuate or rounded and is adapted to receive the pin 60. The ledge 84 holds or snugs the pin portion 60 in place by frictional engagement while still allowing the pin portion 60 to rotate within the opening 74 and against the bottom 86. The hook portion 82 has a height which is less than the height of the central portion 62. Additionally, the spline 70 is shown to comprise a central portion 88 with the ribs 72 and 76 extend out from the central portion 88. The ribs 72 and 76 help to reinforce the central portion 88 and the ribs 72 and 76 and the central portion 88 connect the ball 68 to the central portion 62 of the member 24. The ribs 72 and 76 and the central portion 88 each have a height and the height of each of the ribs 72 and 76 is less than the height of the central portion 88. A side of the member 24 which has the upper rib 72 is referred to as a top side of the member 24 and a side of the member 24 which has the bottom rib 76 is referred to as bottom side of the member 24. The opening 74 is therefore on the bottom side of the member 24. In essence, when the members 24 and 26 are connected together, the top sides are on the same side and the bottom sides of the member 24 and 26 are on the same side.

With particular reference now to FIG. 7, the mounting 28 is shown to have the tongue 34 and the cup portion 78. The tongue 34 is connected to a wall portion 90. The tongue 34 and the wall portion 90 are T-shaped. The mounting 28 further comprises a side 92 with the side 92 having an extension 94 which is used to help retain the ball 68 (not shown) when the ball 68 is seated within the cup portion 78. The side 92 is integrated with the wall 90 with both the wall 90 and the side 92 forming the cup portion 78. The mounting 28 may be constructed of the same material of which the members 28 and 30 are constructed. Further, the mounting 30 is identical to the mounting 28.

FIG. 8 depicts a front side view of the member 24 with particular reference being to show that the rib 64 has a width which is less than the central portion 62. The first end 50 is also shown to indicate that the hook portion 82 has a width which is less than the width of the central portion 62. For example, a portion 96 of the central portion 62 may be seen in FIG. 8. The second end 52 has the pin 60 positioned between the outer tine 56 and the inner tine 58. Further, the ball 68 is wider than the central portion 62.

As can be appreciated from the above, the dental casts 12 and 14, when mounted to the articulator 10 can be easily moved or positioned with respect to each other. A technician can manipulate the casts 12 and 14 to rotate, move, or position the casts 12 and 14 in any desired direction or position for reviewing the dental appliance 22 associated with the casts 12 and 14. The articulator 10 may be separated by proper manipulation and separation of the hook portions 82 of the respective members 24 and 26 from the pin portions 60. The retention of the pin portions 60 against the ledge 84 is easily overcome by application of appropriate pressure or force. Additionally, the use of the hook portions 82, the pin portions 60, and the ledges 84 prevent against the members 24 and 26 from sliding apart or unnecessarily disengaging during use or operation of the articulator 10. Further, the articulator 10 mounted to the casts 12 and 14 may be shipped or transported back to a dentist for manipulation or confirmation by the dentist. As discussed previously, when the members 24 and 26 are connected together, both the top sides of the members 24 and 26 are lined up with each other and both of the bottom sides of the members 24 and 26 are also lined up with each other.

Referring now to FIG. 9, a bottom view of another embodiment of a member 100 is illustrated. The member 100 has a first end 102 and a second end 104. The first end 102 comprises a fork member 106 having an outer tine 108 and an inner tine 110 with a pin member 112 positioned between the tines 108 and 110. The member 100 further comprises a central portion 114 and a reinforcing rib 116. A ball 118 is centered on the central portion 114 of the member 100 and the ball 118 is connected to the central portion 114 by use of a spline 120. One difference between the member 100 and the other members 24 and 26 is that the spline 120 does not have an upper or a lower reinforcing rib. The member 100 is generally C-shaped and may be constructed from a resilient flexible material, such as plastic. Although now shown, the ball 118 is adapted to receive one of the mountings 28 or 30. Additionally, two of the members 100 may be connected together to form a complete articulator.

FIG. 10 depicts a side view of the second end 104 of the member 100. The second end 104 has a hook portion 122 having an opening 124. The opening 124 further has a retaining ledge or portion 126 which is used to capture and retain the pin portion 112 of the first end 102. The opening 124 has a bottom 128 which is arcuate or rounded and is adapted to receive the pin 112. The ledge 126 holds or retains the pin 112 in place by frictional engagement while still allowing the pin portion 112 to rotate within the opening 124 and against the bottom 128. The hook portion 122 has a front portion 130 which has a height which is equal to the height of the central portion 114. The hook portion 122 further has a bottom portion 132 which extends out from the central portion 114. The bottom portion 132 has a width which is greater than the width of the central portion 114. The bottom portion 132 adds strength to the hook portion 122. The spline 120 is illustrated connecting the ball 118 to the central portion 114. The member 100 is similar in design, function, and construction as the members 24 and 26 with the principal differences being that the member 100 does not have any reinforcing ribs associated with the spline 120 and the hook portion 122 has a bottom portion 132 which extends out from the central portion 114 and a front portion 130 having a height equal to the central portion 114.

It should be recognized that the articulator 10 of the present invention can be constructed of various materials and can be assembled from the separable members 24 and 26 or two member 100. Preferably, the articulator 10 will be of relatively lightweight material so that it can be easily constructed, assembled, positioned, secured in place, and removed. Further, the articulator 10 will be constructed of relatively inexpensive materials which will provide for the articulator 10 to be disposable or suitable for one time use.

From all that has been said, it will be clear that there has thus been shown and described herein an articulator which fulfills the various objects and advantages sought therefor. It will become apparent to those skilled in the art, however, that many changes, modifications, variations, and other uses and applications of the subject articulator are possible and contemplated. All changes, modifications, variations, and other uses and applications which do not depart from the spirit and scope of the invention are deemed to be covered by the invention, which is limited only by the claims which follow.

What is claimed is:

1. An articulator for positioning a pair of dental casts relative to each other, the articulator comprising a pair of members adapted to being connected to each other for pivotal movement relative to each other, each member comprising a central portion having a hooked end and a forked end with the forked end having an outer tine, an inner tine and a pin connected between the tines, a reinforcing rib positioned on the central portion, the reinforcing rib spanning between the inner tine and the hooked end, and a ball connected to the central portion by a spline.

2. The articulator of claim 1 wherein the reinforcing rib is asymmetrical on the central portion.

3. The articulator of claim 1 wherein the spline further comprising an upper rib, a central portion, and a lower rib.

4. The articulator of claim 1 wherein the pin is located toward the front of the tines.

5. The articulator of claim 1 wherein the ball is centrally positioned on the member.

6. The articulator of claim 1 wherein the hooked end further comprises a retaining ledge which is adapted to capture the pin once the pin is hooked into the hooked end.

7. The articulator of claim 1 further comprising a pair of mounting members, the mounting members being mountable to each of the dental casts and the mounting members comprising a cup portion for receiving the ball.

8. The articulator of claim 1 wherein the central portion has a height and the hooked end has a hook portion having a height with the height of the central portion being greater than the height of the hook portion.

9. An articulator for positioning a pair of dental casts relative to each other, the articulator comprising:
   a pair of members adapted to being connected to each other for pivotal movement relative to each other, each member comprising a central portion having a hooked end and a forked end with the forked end having an outer tine, an inner tine and a pin connected between the tines, the hooked ends for connecting to the pins of the forked ends;
   a ball connected to each of the central portions by a spline; and
   a reinforcing rib positioned on the central portion, the reinforcing rib spanning between the inner tine and a point prior to the hooked end.

10. The articulator of claim 9 wherein central portion has a height and the hooked end has a bottom portion having a height with the height of the central portion being less than the height of the bottom portion.

11. The articulator of claim 9 wherein the spline further comprising an upper rib, a central portion, and a lower rib.

12. The articulator of claim 9 wherein the central portion has a height and the hooked end has a front portion having a height with the height of the central portion being equal to the height of the front portion.

13. The articulator of claim 9 wherein the ball is centrally positioned on the member.

14. The articulator of claim 9 wherein the hooked end further comprises a retaining ledge which is adapted to capture the pin once the pin is hooked into the hooked end.

15. The articulator of claim 9 wherein central portion has a height and the hooked end has a hook portion having a height with the height of the central portion being greater than the height of the hook portion.

16. The articulator of claim 9 further comprising a reinforcing rib positioned on the central portion, the reinforcing rib being asymmetrical about the central portion.

17. An articulator for positioning a pair of dental casts relative to each other, the articulator comprising:
   a pair of members adapted to being connected to each other for pivotal movement relative to each other, each member comprising a central portion having a hooked end and a forked end with the forked end having an outer tine, an inner tine and a pin connected between the tines, the hooked ends for connecting to the pins of the forked ends, the central portion further comprising a reinforcing rib which spans between the inner tine and a point prior to the hooked end; and
   a ball connected to each of the central portions by a spline with the ball being centered on the member.

18. The articulator of claim 17 wherein the spline further comprising an upper rib, a central portion, and a lower rib.

19. The articulator of claim 17 wherein the hooked end further comprises a retaining ledge which is adapted to capture the pin once the pin is hooked into the hooked end.

20. The articulator of claim 17 wherein the central portion has a thickness and the reinforcing rib has a thickness with the thickness of the central portion being greater than the thickness of the reinforcing rib.

* * * * *